(12) United States Patent
Schönberger et al.

(10) Patent No.: US 9,572,868 B2
(45) Date of Patent: *Feb. 21, 2017

(54) FAST-SETTING ALKOXYSILANE SPRAY FOAMS

(71) Applicant: Bayer Intellectual Property GmbH, Monheim (DE)

(72) Inventors: Jan Schönberger, Haan (DE); Sebastian Dörr, Düsseldorf (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/347,692

(22) PCT Filed: Sep. 24, 2012

(86) PCT No.: PCT/EP2012/068793
§ 371 (c)(1),
(2) Date: Mar. 27, 2014

(87) PCT Pub. No.: WO2013/045403
PCT Pub. Date: Apr. 4, 2013

(65) Prior Publication Data
US 2014/0234284 A1    Aug. 21, 2014

(30) Foreign Application Priority Data
Sep. 29, 2011  (EP) .................... 11183212

(51) Int. Cl.
| | |
|---|---|
| C08G 18/48 | (2006.01) |
| A61K 38/30 | (2006.01) |
| A61L 15/26 | (2006.01) |
| A61L 15/42 | (2006.01) |
| C08G 18/72 | (2006.01) |
| C08G 18/73 | (2006.01) |
| C08G 18/75 | (2006.01) |
| C08G 18/08 | (2006.01) |
| C08G 18/28 | (2006.01) |
| C08G 18/40 | (2006.01) |
| C08G 18/42 | (2006.01) |
| C08G 18/44 | (2006.01) |
| A61K 31/192 | (2006.01) |
| A61K 31/616 | (2006.01) |
| A61K 36/04 | (2006.01) |
| A61K 36/05 | (2006.01) |
| A61K 36/28 | (2006.01) |
| A61K 36/82 | (2006.01) |
| A61K 36/886 | (2006.01) |
| A61K 38/18 | (2006.01) |
| A61K 38/19 | (2006.01) |
| A61K 38/43 | (2006.01) |
| B65D 83/14 | (2006.01) |
| C08G 101/00 | (2006.01) |

(52) U.S. Cl.
CPC ............ *A61K 38/30* (2013.01); *A61K 31/192* (2013.01); *A61K 31/616* (2013.01); *A61K 36/04* (2013.01); *A61K 36/05* (2013.01); *A61K 36/28* (2013.01); *A61K 36/82* (2013.01); *A61K 36/886* (2013.01); *A61K 38/1841* (2013.01); *A61K 38/1858* (2013.01); *A61K 38/191* (2013.01); *A61K 38/43* (2013.01); *A61L 15/26* (2013.01); *A61L 15/425* (2013.01); *B65D 83/752* (2013.01); *C08G 18/0828* (2013.01); *C08G 18/283* (2013.01); *C08G 18/4018* (2013.01); *C08G 18/4238* (2013.01); *C08G 18/44* (2013.01); *C08G 18/4804* (2013.01); *C08G 18/4833* (2013.01); *C08G 18/4854* (2013.01); *C08G 18/722* (2013.01); *C08G 18/73* (2013.01); *C08G 18/755* (2013.01); *C08G 2101/0008* (2013.01); *C08G 2150/50* (2013.01)

(58) Field of Classification Search
CPC .............. C08G 18/289; C08G 65/2639; C08G 18/4837; C08G 18/73; C08G 18/4238; C08G 18/10; C08G 18/4833; C08G 2101/0008; C08G 2150/50; C08L 83/04; A61L 15/425; A61L 15/26
See application file for complete search history.

(56) References Cited

U.S. PATENT DOCUMENTS

| | | | |
|---|---|---|---|
| 6,020,389 A | 2/2000 | Hoheneder | |
| 6,054,499 A | 4/2000 | Pauls et al. | |
| 2004/0072921 A1 | 4/2004 | Stanjek et al. | |

(Continued)

FOREIGN PATENT DOCUMENTS

| | | | |
|---|---|---|---|
| DE | 4303848 A1 | 8/1994 | |
| EP | 1829908 A1 | 9/2007 | |

(Continued)

OTHER PUBLICATIONS

International Search Report for PCT/EP2012/068793 mailed Nov. 21, 2012.

*Primary Examiner* — John Cooney
(74) *Attorney, Agent, or Firm* — Drinker Biddle & Reath LLP

(57) ABSTRACT

The present invention relates to an isocyanate-free multi-component system, in particular for medical uses such as foamable wound coverings, with at least two separate components, wherein the first component comprises at least one alkoxysilane-terminated prepolymer and the second component comprises an aqueous component, wherein the aqueous component is a polyurethane dispersion.

9 Claims, No Drawings

(56) References Cited

U.S. PATENT DOCUMENTS

| | | |
|---|---|---|
| 2004/0204539 A1* | 10/2004 | Schindler et al. ............ 524/588 |
| 2006/0084711 A1 | 4/2006 | Stanjek et al. |
| 2007/0167598 A1* | 7/2007 | Stanjek et al. ................. 528/25 |
| 2009/0018480 A1 | 1/2009 | Mager et al. |
| 2011/0275728 A1 | 11/2011 | Schonberger et al. |
| 2013/0161352 A1 | 6/2013 | Bodet et al. |
| 2013/0168413 A1 | 7/2013 | Bodet et al. |

FOREIGN PATENT DOCUMENTS

| | | |
|---|---|---|
| EP | 2014314 A1 | 1/2009 |
| WO | WO-00/04069 A1 | 1/2000 |
| WO | WO-02/066532 A1 | 8/2002 |
| WO | WO-2004104078 A1 | 12/2004 |
| WO | WO-2010083953 A1 | 7/2010 |
| WO | PCT/EP2011/063909 | 2/2012 |
| WO | PCT/EP2011/063910 | 2/2012 |
| WO | WO-2012022685 A1 | 2/2012 |
| WO | WO-2012022686 A1 | 2/2012 |

* cited by examiner

FAST-SETTING ALKOXYSILANE SPRAY FOAMS

RELATED APPLICATIONS

This application is a national stage application (under 35 U.S.C. §371) of PCT/EP2012/068793, filed Sep. 24, 2012, which claims benefit of European Application No. 11183212.7, filed Sep. 29, 2011, which is incorporated by reference herein.

The present invention relates to an isocyanate-free multicomponent system, more particularly for producing foams for medical products such as wound dressings. The invention further relates to a shaped article obtainable from a multicomponent system of this type, and to a multichamber pressurized can filled with a multicomponent system of this type.

Sprayable multicomponent systems are known from the prior art. There are, for instance, sprayable in-situ foams for filling cavities, as for example in the building construction sector. They find particular application in the filling of gaps and voids between frames of windows and doors and the surrounding brickwork, and are notable for good dampproofing properties as well as good thermal insulation properties. Sprayable multicomponent systems of this type are further used to insulate pipework lines or to fill cavities in technical equipment.

These aforementioned in-situ foams are typically polyurethane (PU) foams. These foams are based on compositions which consist of uncrosslinked prepolymers having a large number of free isocyanate groups. Free isocyanate groups are very reactive in that normal ambient temperature is sufficient to cause them to react with each other in the presence of water/moisture to construct a polymeric network from the prepolymers. Alcohols having two or more OH groups, corresponding thiols, and also primary or secondary amines, and mixtures of these, are also possible co-reactants for the aforementioned isocyanates, as well as the atmospheric humidity. Polyols are particularly common for this use. The reaction with polyols/water gives rise to urethane/urea units which can form hydrogen bonds and so are able to form partly crystalline structures in the cured foam. Foam hardness, compressive strength, and tensile strength are all enhanced as a result.

The multicomponent systems are frequently put into pressurized cans and are provided with a propellant to facilitate the foaming-up of the prepolymers as they exit from the pressurized can. In addition, the isocyanate groups of the prepolymer react with the atmospheric humidity to evolve carbon dioxide, which likewise contributes to the foaming. In this reaction, the isocyanate groups involved are converted into amines, which in turn can react with further isocyanate groups to form a polymeric network i.e. are not lost from the crosslinking reaction.

The polyurethane compositions can be manufactured as 1K foams or else as two-component (2K) foams. While 1K foams need only the influence of atmospheric humidity for curing, 2K foams involve separate storage of an isocyanate component and of a polyol component and their mixing with each other only immediately before discharge. This mixing process takes place, in one alternative, in the pressurized body of the pressurized can, the contents of which then have to be fully used up speedily, since the polymerization reaction takes place irrespective of whether the foam is or is not discharged. Systems of this type are therefore frequently also referred to as 1.5K foams.

Another possibility is to use a two-chamber pressurized can, where the two components are mixed with one another only in the region of the outlet valve. The main advantage of the 2K foams over the 1K foams lies in the appreciably faster curing reaction, since it takes place even in the absence of atmospheric humidity. By contrast, the curing rate with 1K foams is determined by the atmospheric humidity and also by the rate at which the atmospheric humidity diffuses into the foamed material.

The aforementioned multicomponent systems typically include, in addition to the prepolymer components, further auxiliaries as well, such as foam stabilizers, for example, and also catalysts intended to accelerate the crosslinking reaction. Used primarily among the latter are organotitanium or organotin compounds, such as dibutyltin dilaurate, for example.

In the fully cured state, the polyurethane foams specified above possess good mechanical and heat insulation properties and adhere very well to the majority of substrates. However, the aforementioned polyurethane foams may still comprise monomeric diisocyanates, an undesirable phenomenon in the context of the use of the foams for wound treatment.

In order to reduce the hazard potential of the aforementioned spray foams, DE 43 03 848 A1 describes prepolymers which either contain no monomeric isocyanates or have only low concentrations at most of these compounds. Here, however, there is a certain risk that the prepolymer may still have free isocyanate groups, which is again undesirable for medical applications.

Polymerizable foamable compositions which do not cure via free isocyanate groups have been developed in recent years for the aforementioned reasons. U.S. Pat. No. 6,020,389 A1, for instance, discloses silicone foams comprising alkoxy-, acyloxy-, or oximo-terminated silicone prepolymers. These compounds polymerize via condensation reaction of siloxane groups. These compounds are disadvantageous because of their long curing time, since they—like the 1K polyurethane spray foams—are reliant on atmospheric humidity for the polymerization reaction. Full reaction accordingly takes a long time, with comparatively thick foamed layers in particular. This is not just inconvenient, but also problematic in that the foam structure formed by the spraying undergoes partial collapse again before the pore walls may have developed sufficient strength of their own through the ongoing polymerization reaction.

WO 00/04069 discloses alkoxysilane-terminated polyurethane prepolymers. These prepolymers possess a conventional polyurethane backbone, which is obtained in a conventional manner by reaction of difunctional isocyanates with polyols. An excess of polyfunctional isocyanates is used to ensure that the respective end groups of the prepolymer chains possess free isocyanate groups. These isocyanate-terminated prepolymers are then reacted in a further reaction step with an aminoalkyltrialkoxysilane to give the desired alkoxysilane-terminated polyurethane prepolymers. Aminopropyltrimethoxysilane is used for this purpose, in particular. The prepolymer obtained therefrom bears trimethoxysilane-terminated end groups coupled to the polyurethane backbone via a propylene spacer. Owing to the propylene group between the silicon atom and the polyurethane backbone, silanes of this type are also referred to as γ-silanes.

In the curing reaction, the γ-silanes react with water to eliminate alcohol and thereby form Si—O—Si networks, curing the prepolymer. Both the γ-silanes and the isocyanate-terminated polyurethane prepolymers have the disadvantage of comparatively slow progress of the curing reaction. This disadvantage can be compensated only partly by admixing γ-silane-based compositions with large amounts of crosslinking catalysts, such as the dibutyltin dilaurate also used for polyurethane prepolymers, for example. This, however, has a deleterious effect on the shelf-life of such compositions in some instances.

Since even comparatively large amounts of crosslinking catalyst cannot fully compensate the low reactivity of γ-silanes, more reactive types of compounds have been sought. Such compounds are known from WO 02/066532 A1 for example. The prepolymers described therein are again silane-terminated polyurethane prepolymers. The essential difference from the γ-silanes described previously is that a methylene spacer, rather than the propylene group, has been inserted between the polyurethane backbone and the silicon atom. This is why the silanes are also referred to as α-silanes. The shorter distance from the silicon atom to the highly polar urea group of the polyurethane backbone increases the reactivity of the alkoxy groups on the silicon atom (α-effect), so the hydrolysis of the alkoxysilane groups and the subsequent condensation reaction proceeds at an appreciably increased rate.

A disadvantage affecting both α-silanes and γ-silanes, though, is that producing sprayable foams from these prepolymers is extremely difficult. In particular, the provision of a spray foam that can be dispensed from pressurized cans, and that is to generate a loose pore structure with large pore volume, is virtually unrealizable. The reason for this is that, in contrast to the polyurethane foams, the action of water during the crosslinking reaction does not produce gaseous reaction products (such as $CO_2$ with the polyurethane foam); instead, alcohols are eliminated, such as methanol or ethanol, for example. Unlike a gaseous reaction product, however, these compounds are not able to develop foaming effects, and so a foam sprayed from a pressurized can collapses in on itself substantially prior to curing. The possibility of countering this effect by the use of foam stabilizers, moreover, is limited.

This problem is addressed by EP 1 829 908 A1, which proposes a 2K silane prepolymer-based system. In this system, in a first component, use is made of the silane prepolymer, such as a silane-terminated polyurethane prepolymer, for example, dibutyltin dilaurate as catalyst, and also relatively large amounts than calcium carbonate. The second component consists of a highly concentrated aqueous solution of citric acid. For the foaming of this 2K foam, the two components are mixed with one another and discharged at the desired location via a spray applicator. With this system, the water present in the second component brings about the crosslinking reaction of the silane prepolymer, and the calcium carbonate, under the action of the highly concentrated citric acid solution, releases $CO_2$. As known from polyurethane prepolymers, the carbon dioxide brings about foaming of the discharged prepolymer mixture.

This system, however, carries the disadvantage that the highly concentrated citric acid solution possesses a pH of around 1-2 and consequently develops caustic or at least irritant properties. Particularly in the event of spraying from pressurized cans, an aerosol may be formed, thereby irritating the eyes, the skin, and—not least—the respiratory tract of the user. Moreover, the caustic or corrosive potential of the citric acid imposes considerable limits on the scope for application of the compositions. It is inconceivable, for example, for such compositions to be applied directly to the skin as a sprayable wound dressing in the medical sector, especially to an injured skin site or an injured body part.

Against this background, the object of the present invention is that of modifying a multicomponent system of the type specified at the outset in such a way that it can be used to produce spray foams which cure rapidly, exhibit a highly porous structure with a high pore volume, and allow a fairly broad field of application. The composition is also to pose a minimal hazard potential to the user, and is also, more particularly, to be suitable for the production of sprayable wound dressings.

This object is achieved by means of an isocyanate-free multicomponent system, more particularly for producing foams for medical products such as wound dressings, having at least two separate components, the first component comprising at least one alkoxysilane-terminated prepolymer and the second component comprising an aqueous component, with the aqueous component comprising a polyurethane dispersion.

Isocyanate-free in the present context refers to a system that contains less than 0.5 wt % of isocyanate-containing components.

Surprisingly it has transpired that by using an aqueous polyurethane dispersion, such a multicomponent system can be dispensed in a multichamber pressurized can, with the polyurethane dispersion having the effect of dissolving a series of commercial propellant gases in the aqueous phase. This prevents phase separation between propellant gas and the second component. In addition, the solubility of these propellant gases in the first component, comprising the prepolymer, tends to be less problematic. Accordingly, the propellant gas and the first component, and/or the propellant gas and the second component, are present in a very largely homogeneous mixture before they exit the pressurized can. After the mixing of the two, first and second, components held separately in the can, in a mixing nozzle of the pressurized can, the propellant gas dissolved in the mixture causes substantial expansion of this mixture after exit from the pressurized can, thus producing a fine-cell foam. In other words, the present invention provides a 2K silane foam system from which polymer foams of high pore volume are obtainable, without any need for additional use of gas-evolving reactants, such as the combination of calcium carbonate and citric acid, for example.

The multicomponent system of the invention can be employed for a multiplicity of applications. It is suitable, for instance, for all fields of application in which the aforementioned polyurethane foams and also α-/γ-silane foams are proposed, such as for the building construction sector, for the insulation of pipes, or else for the filling of cavities in machines.

It has, surprisingly, further transpired that the multicomponent system of the invention can also be used in the medical sector, since it contains no toxic or irritant compounds.

The medical field of use includes in this case, for example, the provision of wound dressings preparable in situ. For this, the multicomponent system of the invention, after the mixing of the two components, can be sprayed, or otherwise applied, to skin injuries or injuries of some other kind. The foamed compositions exhibit no marked adherence to organic tissue such as wound tissue, for example, and their porous structure additionally enables them to absorb wound secretions or blood. The reason for this appears to be that the multicomponent system of the invention, when spray-dispensed under the aforementioned conditions, forms an open porous structure, to some extent at least, and hence is absorbent.

A further advantage of the multicomponent system of the invention is observed, in the aforementioned medical applications, also in the possibility for varying the hardness of the resultant polymer foam through the choice of the chemical nature and/or the chain length of the polymer backbone of the silane prepolymer. In addition to the aforementioned parameters, other measures too may be used to modify the hardness of the foam, such as via the degree of crosslinking, for example. It is possible, accordingly, to form very soft and hence yielding polymer foams, or else firm polymer foams with support qualities. The medical field of use, accordingly, is not confined only to direct wound treatment; instead, the immobilization of limbs is possible as well, in cases, for example, of bone fractures, ligament strains, sprains, and the like. Furthermore, applications in the cosmetic sector are likewise conceivable.

Although the provision of the multicomponent system of the invention in pressurized cans represents a convenient possibility, the invention is nevertheless not confined to this. Accordingly, the multicomponent system of the invention may also readily be used—after the mixing of the two components—as a pouring composition.

The silane-terminated prepolymer present in the first component in accordance with the invention may in principle comprise all types of polymer backbones, and also mixtures thereof as well.

According to one preferred embodiment, the alkoxysilane-terminated prepolymer comprises an alkoxysilane-terminated polyurethane prepolymer. The polyurethane backbone in this case may have a variety of constructions. Thus, on one hand, it is possible to produce a polymer backbone by reaction of diisocyanates with diols, giving the polymer backbone a multiplicity of internal urethane groups. The terminal isocyanate groups resulting from the reaction regime are subsequently reacted with aminoalkylalkoxysilanes. In this way, silane-terminated prepolymers are obtained, and depending on chain length permit the production of comparatively firm foams.

A polyurethane prepolymer in the sense of the present invention also comprehends a polymer backbone which in its main chain has, for example, only polyetherpolyols and/or polyesterpolyols, and which carries isocyanate groups at its chain ends. A polymer backbone of this kind is suitable more particularly for medical applications, since the corresponding silane-terminated prepolymer has a sufficiently low viscosity, and so is easily foamed. In contrast, urethane groups or urea groups in the polymer backbone are less preferred, since they increase the viscosity, considerably so in some cases.

According to one particularly preferred embodiment of the invention, the alkoxysilane-terminated prepolymer may comprise an alkoxysilane-terminated polyurethane prepolymer, which is prepared more particularly from an aminoalkoxysilane and an isocyanate-terminated prepolymer, it being possible for the isocyanate-terminated prepolymer to have been prepared, more particularly, from a polyol and an aliphatic polyisocyanate.

To obtain silane-terminated polyurethane prepolymers of low viscosity, it is particularly advantageous, furthermore, to prepare the isocyanate-terminated prepolymers by reacting an excess of the isocyanate component with the polyol component and then removing the unreacted portion of isocyanate component, preferably by thin-film distillation. The reaction, with alkoxysilanes, of the isocyanate-terminated prepolymer prepared and purified in this way yields silane-terminated prepolymers of particularly low viscosity.

Polyetherpolyols which can be used in accordance with the invention are, for example, the polytetramethylene glycol polyethers which are known per se in polyurethane chemistry and are obtainable, for example, by polymerization of tetrahydrofuran by means of cationic ring opening. Likewise suitable are the known conventional adducts of styrene oxide, ethylene oxide, propylene oxide, butylene oxides and/or epichlorohydrin with starter molecules having a functionality of two or more. Starter molecules that can be used in this context are all compounds known from the prior art, such as, for example, water, butyldiglycol, glycerol, diethylene glycol, trimethyolpropane, propylene glycol, sorbitol, ethylenediamine, triethanolamine and 1,4-butanediol. Preferred starter molecules are water, ethylene glycol, propylene glycol, 1,4-butanediol, diethylene glycol and butyldiglycol.

Another advantage of the polyether- and/or polyesterpolyols in the polymer backbone is that in this way the hydrophilicity of the resultant foam can be adapted to requirements, giving this foam, for example, improved absorbency for aqueous fluids, such as blood or wound secretions. It is nevertheless useful in this case not to set the fraction of ethylene oxide units in the polyetherpolyol at too high a level, since this would otherwise lead to severe swelling of the wound dressing. Consequently, one preferred embodiment of the multicomponent system of the invention is defined such that the fraction of ethylene oxide units in the polyetherpolyol is not more than 50 wt % preferably not more than 30 wt %, more preferably not more than 20 wt %. The lower limit of ethylene oxide groups may be situated, for example, at about 5 wt %. Regardless of this, it is also possible to use polyetherpolyols without ethylene oxide units.

As far as the polyester units are concerned, they may be monofunctional or polyfunctional, more particularly difunctional.

The polyetherpolyols and/or polyesterpolyols which can be used for the purposes of the present invention may be constructed of aliphatic units or else may also possess aromatic groups. Conversely, in relation to the isocyanates or polyfunctional isocyanates employed, it is particularly preferred for them to have only aliphatic groups. In other words, in accordance with the invention, preferably no aromatic isocyanates are employed.

Suitable in principle for preparing the alkoxysilane-terminated prepolymer of the invention are the aromatic, araliphatic, aliphatic or cycloaliphatic polyisocyanates with an NCO functionality of ≥2 that are known per se to the skilled person. Examples of such polyisocyanates are 1,4-butylene diisocyanate, 1,6-hexamethylene diisocyanate (HDI), isophorone diisocyanate (IPDI), 2,2,4 and/or 2,4,4-trimethylhexamethylene diisocyanate, the isomeric bis(4,4'-isocyanatocyclohexyl)methanes or their mixtures of any desired isomeric content, 1,4-cyclohexylene diisocyanate, 1,4-phenylene diisocyanate, 2,4- and/or 2,6-tolylene diisocyanate, 1,5-naphthylene diisocyanate, 2,2'- and/or 2,4'- and/or 4,4'-diphenylmethane diisocyanate, 1,3- and/or 1,4-bis(2-isocyanatoprop-2-yl)benzene (TMXDI), 1,3-bis(isocyanatomethyl)benzene (XDI), alkyl 2,6-diisocyanatohexanoate (lysine diisocyanates) with C1-C8 alkyl groups, and also 4-isocyanatomethyl-1,8-octane diisocyanate (nonane triisocyanate) and triphenylmethane 4,4',4"-triisocyanate.

In addition to the polyisocyanates referred to above, modified diisocyanates or triisocyanates of uretdione, isocyanurate, urethane, allophanate, biuret, iminooxadiazinedione and/or oxadiazinetrione structure may also be used proportionally.

The compounds in question are preferably polyisocyanates or polyisocyanate mixtures of the abovementioned kind with exclusively aliphatically and/or cycloaliphatically attached isocyanate groups and with an average NCO functionality for the mixture of 2 to 4, preferably 2 to 2.6 and more preferably 2 to 2.4.

According to one particularly preferred embodiment of the multicomponent system of the invention, the alkoxysilane-terminated prepolymer comprises α-silane groups. Provision is also made in this context for the alkoxysilane-terminated prepolymer present in the composition of the invention to have exclusively α-silane groups.

By an α-silane group is meant, as already observed above, that a methylene spacer is present between the silicon atom and the polymer backbone. Such silanes are notable for particular reactivity in relation to the condensation reaction. Because of this, it is possible in the context of the present invention to forgo entirely the use of heavy metal-based crosslinking catalysts such as organic titanates or organic tin(IV) compounds. This is an advantage especially in the case of medical fields of use for the multicomponent system of the invention.

With further preference the α-silane groups of the alkoxysilane-terminated prepolymer used are triethoxy-α-silane groups. This is of advantage in that comparatively safe ethanol is released during the crosslinking reaction, instead of methanol in the case of the frequently used methoxy-α-silanes. Although the reactivity and hence curing rate of the trimethoxy-α-silanes is higher than that of the triethoxy-α-silanes, the reactivity of the triethoxy-α-silanes is sufficiently high for the mixture to cure fully within a few minutes, even in some cases after less than one minute.

It is likewise preferred for the α-silane groups of the alkoxysilane-terminated prepolymer used to be diethoxy-a-silane groups.

With further preference, the weight average of the alkoxysilane-terminated prepolymer is 500 to 20 000 g/mol, preferably 500 to 6000 g/mol, more particularly 2000 to 5000 g/mol. The aforementioned molecular weights are of advantage in particular in relation to polyetherpolyols and polyesterpolyols; the cured compositions of the invention that can be produced from them may be adjusted alternatively from very soft to very firm. If, for example, very soft cured compositions are required, it is an advantage for the weight average of the alkoxysilane-terminated prepolymer with a polyetherpolyol to be more than 2000 g/mol, preferably up to 20 000 g/mol, more particularly at least 3000 g/mol, more preferably at least 3200 g/mol, very preferably 3500 to 6000 g/mol. For producing cured compositions of comparable strength using prepolymers with polyesterpolyols, a weight average of the alkoxysilane-terminated prepolymer of up to 2000 g/mol, more particularly from 300 up to 1500 g/mol, is sensible.

The average molecular weight of the polyols is determined as follows: First of all, the OH number is determined experimentally by esterification and subsequent back-titration of the excess esterifying reagent with alcoholic potassium hydroxide standard solution. The OH number is reported in mg of KOH per gram of polyol. From the OH number, the average molecular weight is calculated via the formula average molecular weight=56×1000×OH functionality/OH number.

For the purposes of the present invention, provision is made for the second, aqueous component to be a polyurethane dispersion. This means for the purposes of the present invention that, for example, a commercial polyurethane dispersion can be used whose concentration, however, may also be reduced with additional water. As polyurethane dispersion it is possible in principle to use all polyurethane dispersions available on the market. Here as well, however, it is advantageous to use polyurethane dispersions which have been prepared from aromatic-free isocyanates, since these are less objectionable particularly for medical applications. The polyurethane dispersion, moreover, may also include other ingredients. With particular preference, the polyurethane dispersion contains 5 to 65 wt % of polyurethane, more particularly 20 to 60 wt %.

In a development of the multicomponent system of the invention, the weight average of the polyurethane in the polyurethane dispersion is 10 000 to 1 000 000 g/mol, more particularly 20 000 to 200 000 g/mol, determined in each case via gel permeation chromatography against a polystyrene standard in tetrahydrofuran at 23° C. Polyurethane dispersions with such molar masses are particularly advantageous since they represent shelf-stable polyurethane dispersions which, moreover, produce high solubility of the propellant gas in the second component on dispensing into pressurized cans.

With further preference the polyurethane dispersion possesses a pH of 5.0 to 9.0. This is particularly advantageous since polyurethane dispersions in this pH range have the effect, first, of accelerating the condensation reaction of the silane-terminated prepolymer. Moreover, this preferred pH range is also acceptable physiologically, and so such compositions can also be employed in medical fields of application. For applications directly on the skin or on wounds it is particularly advantageous to provide a pH for the polyurethane dispersion that is in the vicinity of the pH of human skin, in other words, for example, from 5.0 to 7.0, especially preferably at about pH 5.5.

For the polyurethane dispersions, the aforementioned pH levels can be set in a variety of ways. For instance, the polyurethane dispersion may be admixed, for example, with an acid, a base, or a buffer, the respective amounts of these substances that are employed being selected such that the desired pH is achieved. A further advantage of the aforementioned pH levels, moreover, is that within these ranges there is generally no coagulation of the polymer particles in the polyurethane dispersion—in other words, under these conditions, the dispersion is stable on storage.

In accordance with one particularly preferred embodiment of the multicomponent system of the invention, the first and/or the second component comprises an active medical and/or cosmetic ingredient. The dividing line between these two groups of active ingredients is not sharply defined, since numerous active medical ingredients also have cosmetic effects.

In this context it is likewise conceivable to provide the active ingredient or ingredients in the form of a further component, i.e. third or fourth component, and not to mix them with the first and second components until immediately prior to the application of the multicomponent system. Because of the increase in complexity of the multicomponent system as the number of separate components goes up, however, this route generally makes sense only when the active ingredients employed are incompatible both with the first and with the second component.

The active ingredients may be present as pure active ingredient or else in encapsulated form, in order to achieve a time-delayed release, for example.

Active cosmetic ingredients contemplated include more particularly those which possess skincare qualities, examples being active moisturizing or skin-calming ingredients.

Useful active medical ingredients for the purposes of the present invention embrace a multiplicity of types and classes of active ingredient.

An active medical ingredient of this kind may comprise, for example, a component that releases nitrogen monoxide under in vivo conditions, preferably L-arginine or an L-arginine-containing or L-arginine-releasing component, more preferably L-arginine hydrochloride. Proline, ornithine and/or other biogenic intermediates such as, for example, biogenic polyamines (spermine, spermitine, putrescine or bioactive artificial polyamines) can also be used. Such components are known to augment wound healing, while their continuous, substantially uniform rate of release is particularly conducive to wound healing.

Further active ingredients usable according to the invention comprise at least one substance selected from the group of vitamins or provitamins, carotenoids, analgesics, antiseptics, hemostyptics, antihistamines, antimicrobial metals or salts thereof, plant-based wound healing promoter substances or substance mixtures, plant extracts, enzymes, growth factors, enzyme inhibitors, and combinations thereof.

Suitable analgesics are more particularly nonsteroidal analgesics, especially salicylic acid, acetylsalicylic acid and derivatives thereof such as Aspirin®, aniline and its derivatives, acetaminophen, e.g., Paracetamol®, antranilic acid and derivatives thereof, e.g., mefenamic acid, pyrazole or its derivatives, e.g., methamizole, Novalgin®, phenazone, Antipyrin®, isopropylphenazone, and, very preferably, arylacetic acids and their derivatives, heteroarylacetic acids and their derivatives, arylpropionic acids and their derivatives, and herteroarylpropionic acids and also their derivatives, e.g., Indometacin®, Diclophenac®, Ibuprofen®, Naxoprophen®, Indomethacin®, Ketoprofen®, Piroxicam®.

Growth factors include in particular the following: aFGF (Acidic Fibroplast Growth Factor), EGF (Epidermal) Growth Factor), PDGF (Platelet Derived Growth Factor), rhPDGF-BB (Becaplermin), PDECGF (Platelet Derived Endothelial Cell Growth Factor), bFGF (Basic Fibroplast Growth Factor), TGF α; (Transforming Growth Factor alpha), TGF β (Transforming Growth Factor beta), KGF (Keratinocyte Growth Factor), IGF1/IGF2 (Insulin-Like Growth Factor), and TNF (Tumor Necrosis Factor).

Suitable vitamins or provitamins include more particularly the fat-soluble or water-soluble vitamins vitamin A, group of retinoids, provitamin A, group of carotenoids, especially β-carotene, vitamin E, group of tocopherols, especially α-tocopherol, β-tocopherol, γ-tocopherol, δ-tocopherol, and α-tocotrienol, β-tocotrienol, γ-tocotrienol, and δ-tocotrienol, vitamin K, phylloquinone, especially phytomenadione or plant-based vitamin K, vitamin C, L-ascorbic acid, vitamin B 1, thiamine, vitamin B2, riboflavin, vitamin G, vitamin B3, niacin, nicotinic acid and nicotinamide, vitamin B5, pantothenic acid, provitamin B5, panthenol or dexpanthenol, vitamin B6, vitamin B7, vitamin H, biotin, vitamin B9, folic acid, and combinations thereof.

A useful antiseptic is any such agent that has a gemicidal, bactericidal, bacteriostatic, fungicidal, virucidal, virustatic and/or generally microbiocidal effect.

Especially suitable are those compounds selected from the group of resorcinol, iodine, iodine-povidone, chlorhexidine, benzalkonium chloride, benzoic acid, benzoyl peroxide or cethylpyridinium chloride. Also suitable for use as antiseptics, furthermore, are antimicrobial metals in particular. Antimicrobial metals that can be used include more particularly silver, copper, or zinc, and also their salts, oxides, or complexes, in combination or on their own.

Plant-based active wound healing promoter ingredients in the context of the present invention include more particularly extracts of camomile, hamamelis extracts, e.g., *Hamamelis virgina*, calendula extract, aloe extract e.g., *Aloe vera, Aloe barbadensis, Aloe feroxoder*, or *Aloe vulgaris*, green tea extracts, seaweed extract, e.g., red algae or green algae extract, avocado extract, myrrh extract, e.g. *Commophora molmol*, bamboo extracts, and also combination thereof.

The amount of the active ingredients is guided primarily by the medically required dose and also by compatibility with the other constituents of the composition of the invention.

The multicomponent systems of the invention may further be admixed with other auxiliaries as well. Examples of those contemplated for this purpose include foam stabilizers, thickeners or thixotroping agents, antioxidants, photoprotectants, emulsifiers, plasticizers, pigments, fillers, pack-stabilizing additives, biocides, cosolvents, and/or flow control agents.

Examples of suitable foam stabilizers include alkylpolyglycosides. They are obtainable by techniques known per se to the skilled person, through reaction of relatively long-chain monoalcohols with mono-, di- or polysaccharides (Kirk-Othmer Encyclopedia of Chemical Technology, John Wiley & Sons, Vol. 24, p. 29). The relatively long-chain monoalcohols, which optionally may also be branched, have preferably 4 to 22 C atoms, preferably 8 to 18 C atoms, and preferably 10 to 12 C atoms in an alkyl radical. Specific examples of relatively long-chain monoalcohols include 1-butanol, 1-propanol, 1-hexanol, 1-octanol, 2-ethylhexanol, 1-decanol, 1-undecanol, 1-dodecanol (lauryl alcohol), 1-tetradecanol (myristyl alcohol), and 1-octadecanol (stearyl alcohol). It will be appreciated that mixtures of the stated relatively long-chain monoalcohols may also be used.

These alkylpolyglycosides preferably have structures derived from glucose. Particular preference is given to using alkylpolyglycosides of the formula (I).

Formula (I)

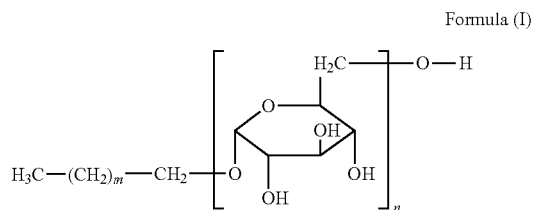

m = 4 to 20
n = 1 or 2

Preferably m is a number from 6 to 20, more preferably 10 to 16.

The alkylpolyglycosides preferably have an HLB value of less than 20, more preferably of less than 16, and very preferably of less than 14, with the HLB value being computed using the formula HLB=20·Mh/M, where Mh is the molar mass of the hydrophilic portion of a molecule and M is the molar mass of the entire molecule (Griffin, W. C.: Classification of surface active agents by HLB, J. Soc. Cosmet. Chem. 1, 1949).

Further foam stabilizers include conventional anionic, cationic, amphoteric, and nonionic surfactants, and also mixtures thereof. Preference is given to using alkylpolyglycosides, EO/PO block copolymers, alkyl or aryl alkoxylates, siloxane alkoxylates, esters of sulfosuccinic acid and/or alkali or alkaline earth metal alkanoates. Particular preference is given to using EO/PO block copolymers.

In addition, to improve the foam properties of the resulting foam, conventional monohydric and polyhydric alcohols, and also mixtures thereof, may be used. These are monohydric or polyhydric alcohols or polyols, such as ethanol, propanol, butanol, decanol, tridecanol, hexadecanol, ethylene glycol, neopentyl glycol, butanediol, hexanediol, decanediol, trimethylolpropane, glycerol, pentaerythritol, monofunctional polyether alcohols and polyester alcohols, polyetherdiols and polyesterdiols.

These foam stabilizers can be added to the first component and/or, preferably, to the second component, provided no chemical reaction takes place with the respective components. The overall amount of these compounds, based on the multicomponent system of the invention, is more particularly 0.1 to 20 wt %, preferably 1 to 10 wt %.

The proportions of the first and second components of the multicomponent system of the invention are advantageously set relative to one another such that polymerization is complete and involves quantitative or near-quantitative conversion of the first component. For example, therefore, the first and second components of the multicomponent system of the invention are present in a volume ratio to one another of 1:10 to 10:1, preferably in a volume ratio to one another of 1:1 to 5:1, more particularly 2:1 to 3:1, more preferably at about 2.5:1.

According to one particularly preferred embodiment of the invention, the first and/or second component(s) of the multicomponent system may each comprise a propellant gas, with the propellant gas being selectable more particularly from the group of dimethyl ether, alkanes, such as propane, n-butane, isobutane, and also mixtures of these. A multicomponent system of this kind is suitable, as already set out earlier on above, to particularly good effect for the production of foams, especially for wound treatment.

The invention also provides the use of a multicomponent system of the invention for producing a foam, more particularly for the treatment of wounds.

The present invention further provides a shaped article, more particularly in the form of a wound dressing, which is obtainable by mixing the first and second components of an isocyanate-free multicomponent system of the invention and by fully polymerizing the resultant mixtures. The shaped article of the invention may be foamed or unfoamed. However, it is preferably a foamed shaped article.

The mixture preferably polymerizes at room temperature within a time of not more than five minutes to completion, preferably within three minutes, more preferably within one minute.

Complete polymerization for the purposes of the present invention is to be understood as meaning more than just a skin having been formed on the outside; that is, more than that the outside surface of the shaped article is no longer tacky, but instead that the prepolymers have very largely undergone complete reaction. This is verified to be the case in the context of the present invention when the shaped article produced is completely indented for some seconds with a finger and then automatically returns to the original state when the pressure of the finger is removed.

Curing with rapidity of this kind is advantageous in medical applications in particular, specifically for use as a wound dressing. This is because it is only the extremely rapid curing that makes it possible in the first place that the wound dressing can be promptly enclosed in a bandage and put under mechanical loading by the patient. Long waiting times can be avoided as a result.

The invention further provides the use of a more particularly foamed shaped article as a wound dressing. An advantage of a wound dressing of this kind is that the foam structure not only allows absorption of wound secretions but also at the same time provides mechanical protection to the wound against knocks and the like. Even the pressure of garments on the wound is partially absorbed by the foam structure.

The sprayed wound dressing further conforms ideally to the usually irregular contours of a wound, thus ensuring a wound covering which is very largely free from pressure pain due to improper wound-dressing fit. In addition, the wound dressing produced in accordance with the invention shortens the time needed for wound care as compared with care using a traditional wound dressing, since there is no need for the time-consuming cutting to size and shape.

The present invention further relates to a multichamber pressurized can having an outlet valve and a mixing nozzle, comprising a multicomponent system of the invention, the first and second components of the multicomponent system being introduced separately into one first chamber and one second chamber of the multichamber pressurized can, and at least one of the chambers being charged with a liquid propellant gas under superatmospheric pressure, in particular with a pressure of at least 1.5 bar. The liquid propellant gas in the chambers may be identical or different. A two-chamber pressurized can particularly suitable for this purpose is known, for example, from the as yet unpublished PCT applications having the application numbers PCT/EP2011/063910 and PCT/EP2011/063909, the content of which is hereby incorporated in full into the present specification.

According to a further embodiment of the multichamber pressurized can of the invention, the propellant gases are soluble in both the first and second components, with the solubility being at least 3 wt % at a filling pressure of at least 1.5 bar and at a temperature of 20° C., and with the amount of propellant gas introduced being, in particular, not more than that which corresponds to the solubility. This ensures that the spray-dispensed foam is of consistent quality, since it is never the case that only propellant gas will escape from one of the chambers at the start of the spraying operation and hence the mixing ratio between first and second components will be nonoptimal.

There is a further advantage in that, owing to the solubility of the propellant gas in the chambers of the pressurized can, no phase separation comes about between first/second components and the propellant gas. Therefore, the propellant gas escapes only when the pressurized can is actuated and the first and second components become mixed, and foams up this mixture in the process. The very rapid curing time of the multicomponent systems of the invention has the effect that the foam structure produced by the propellant gas "freezes" and does not collapse in on itself.

The aforementioned effect is amplified by the use of the polyurethane dispersion (second component) provided in accordance with the invention, since the dispersion to some extent has stabilizing properties on the foam. A propellant gas solubility of at least 3 wt % is advantageous to ensure sufficient foaming of the delivered mixture. The propellant gas content of the first component is preferably from 10 to 40 wt %, more preferably from 15 to 25 wt %, and the propellant gas content of the second component is from 3 to 20 wt %, more preferably 5 to 15 wt %, based in each case on the resulting overall weight of the particular mixture. The amount of propellant gas introduced into the can and/or dissolved in the individual components may also be used to influence the foam structure. Thus, a higher quantity of propellant gas generally leads to a foam of lower density, in the case of a composition.

With particular preference the propellant gas is selected from dimethyl ether, alkanes, such as propane, n-butane, isobutane, and also mixtures of these. These propellant gases are particularly advantageous since it has emerged that they are soluble, both in the first component, which comprises the silane prepolymer and in the second component of the aqueous polyurethane dispersion. Among the propellant gases stated above, the alkanes are especially preferable, since in contrast to dimethyl ether they evoke a less burning sensation to the patient on contact with open wounds.

A further subject of the present invention concerns the use of a multicomponent system of the invention for producing a foamed or unfoamed shaped article, more particularly a sheetlike shaped article such as a wound dressing.

The present invention will now be more particularly elucidated with reference to exemplary embodiments.

EXAMPLES

General:
Any amounts, proportions and percentages hereinbelow are based, unless otherwise stated, on the weight and the overall amount, or the overall weight, of the compositions.

Unless noted otherwise, all analytical measurements relate to measurements at temperatures of 23° C.

Methods:
The solids contents are determined by heating a weighed sample to constant weight at 125° C. At constant weight, the sample is weighed again to ascertain the solids content.

Unless expressly mentioned otherwise, NCO contents were determined volumetrically in accordance with DIN-EN ISO 11909.

Monitoring for free NCO groups was carried out by means of IR spectroscopy (band at 2260 cm$^{-1}$).

The reported viscosities were determined using rotary viscometry in accordance with DIN 53019 at 23° C. with a rotary viscometer at a rotary frequency of 18 s$^{-1}$ from Anton Paar Germany GmbH, Ostfildern, DE.

The mean particle sizes (the number average being indicated) of the polyurethane dispersions were determined after dilution with deionized water by means of laser correlation spectroscopy (apparatus: Malvern Zetasizer 1000, Malvern Inst. Limited).

The storage stability of the dispersions was tested over a period of 6 months after preparation, by storage at room temperature.

The elongation at break was determined in accordance with DIN 53504.

The maximum soluble propellant gas quantity was determined at 20° C. in "test glasses for optical checks on aerosols" from Pamasol Willi Mäder AG, CH. The maximum soluble propellant gas quantity relates to the weight ratio of propellant gas to the substance/mixture under investigation, and was reached as soon as the propellant gas just failed to form a second phase on a permanent basis (>1 h).

The mixtures were foamed up using a 2K spraying apparatus which was filled in the manner described in the PCT applications with the application numbers PCT/EP2011/063910 and PCT/EP2011/063909.

Employed Substances and Abbreviations:
Diaminosulfonate: $NH_2$—$CH_2CH_2$—$NH$—$CH_2CH_2$—$SO_3Na$ (45% strength in water)

HDI: hexamethylene 1,6-diisocyanate

PolyTHF® 2000: polytetramethylene glycol polyol, OH number 56 mg KOH/g, number-average molecular weight 2000 g/mol (BASF AG, Ludwigshafen, DE)

PolyTHF® 1000: polytetramethylene glycol polyol, OH number 112 mg KOH/g, number-average molecular weight 1000 g/mol (BASF AG, Ludwigshafen, DE)

Desmophen® C 2200: linear, aliphatic polycarbonatediol having terminal hydroxyl groups and a molecular weight of about 2000 g/mol, Bayer MaterialScience AG, Leverkusen, DE.

Polyether LB 25: monofunctional polyether based on ethylene oxide/propylene oxide with number-average molecular weight of 2250 g/mol, OH number 25 mg KOH/g (Bayer MaterialScience AG, Leverkusen, DE)

Desmodur® N 3300: HDI trimer, NCO content 21.8±0.3 wt % (Bayer MaterialScience AG, Leverkusen, DE)

Desmodur® XP 2599: aliphatic prepolymer containing ether groups and based on HDI, NCO equivalent weight about 700 g (Bayer MaterialScience AG, Leverkusen, DE)

Desmodur® XP 2617: largely linear NCO prepolymer based on HDI, NCO content 12.5±1.0 wt % (Bayer MaterialScience AG, Leverkusen, DE)

Geniosil® XL 926: [(cyclohexylamino)methyl]triethoxysilane (Wacker Chemie AG, Munich, DE)

P/B 3.5: mixture of propane and isobutane such as to give a gas pressure of 3.5 bar at 20° C.

P/B 4.5: mixture of propane and isobutane such as to give a gas pressure of 4.5 bar at 20° C.

DME: dimethyl ether

Example 1

Preparation of Aqueous Polyurethane Dispersion PUD1

450 g of PolyTHF 1000 and 2100 g of PolyTHF 2000 were heated to 70° C. Then a mixture of 225.8 g of hexamethylene diisocyanate and 298.4 g of isophorone diisocyanate was added and the mixture was stirred at 100-115° C. until the NCO value was slightly below the theoretical value. The completed prepolymer was dissolved with 5460 g of acetone at 50° C. and then a solution of 29.5 g of ethylenediamine, 143.2 g of diaminosulfonate and 610 g of water was metered in. Subsequent stirring time was 15 minutes. This was followed by dispersion by addition of 1880 g of water. The solvent was then removed by vacuum distillation to give a storage-stable dispersion having a solids content of 56%, a particle size of 276 nm and a viscosity of 1000 mPas. Not more than 3.1% of P/B 3.5 could be dissolved in the dispersion (solids content 48%) adjusted to a pH of 5.5 using aqueous citric acid.

Example 2

Preparation of Aqueous Polyurethane Dispersion PUD2

1645 g of PolyTHF 2000, 352.5 g of PolyTHF 1000 and 158.6 g of Polyether LB 25 were heated to 70° C. Then, at 70° C. over the course of 5 minutes, a mixture of 177 g of hexamethylene diisocyanate and 234 g of isophorone diisocyanate was added and the mixture was stirred until the NCO value was slightly below the theoretical value. The completed prepolymer was dissolved with 4560 g of acetone at 50° C. and then a solution of 23.1 g of ethylenediamine, 45.2 g of isophoronediamine and 294 g of water was metered in over the course of 10 minutes. Subsequent stirring time was 10 minutes. This was followed by dispersion by addition of 1650 g of water over the course of 10 minutes. The solvent was then removed by vacuum distillation to give a storage-stable dispersion having a solids content of 49%, a particle size of 255 nm and a viscosity of 420 mPas. A maximum of 20.5% of P/B 4.5 could be dissolved in the dispersion adjusted to a solids content of 30% using water.

Example 3

Preparation of Aqueous Polyurethane Dispersion PUD3

174.3 g of Desmophen C 2000, 37.3 g of PolyTHF 1000, 3.9 g of neopentyl glycol, 34.6 g of polypropylene glycol monobutyl ether having a number-average molar mass of 2500 g/mol, and 18.9 g of Polyether LB 25 were heated to 70° C. Then, at 70° C. over the course of 5 minutes, a mixture of 23.2 g of hexamethylene diisocyanate and 30.7 g of isophorone diisocyanate was added and the mixture was stirred until the NCO value was slightly below the theoretical value. After that, at 70° C., 4.4 g of N-methyldiethanolamine are added. The completed prepolymer was dissolved with 330 g of acetone at 50° C. and then a solution of 4.7 g of isophoronediamine in 8.4 g of acetone and, after 5 minutes, 0.1 g of ethylenediamine in 0.6 g of water was metered in. Subsequent stirring time was 10 minutes. Thereafter 35.3 g of 1-normal hydrochloric acid were added and after a further 5 minutes, over the course of 10 minutes, dispersion was carried out by addition of 740 g of water. The solvent was then removed by vacuum distillation to give a storage-stable dispersion having a solids content of 32%, a particle size of 273 nm and a viscosity of <50 mPas. A maximum of 21.1% of P/B 3.5 could be dissolved in the dispersion.

Example 4

Preparation of Aqueous Polyurethane Dispersion PUD4

159.4 g of PolyTHF 2000, 3.9 g of neopentyl glycol, 34.6 g of polypropylene glycol monobutyl ether having a number-average molar mass of 2500 g/mol, and 118.9 g of Polyether LB 25 were heated to 70° C. Then, at 70° C. over the course of 5 minutes, a mixture of 28.2 g of hexamethylene diisocyanate and 37.3 g of isophorone diisocyanate was added and the mixture was stirred until the NCO value was slightly below the theoretical value. After that, at 70° C., 4.4 g of N-methyldiethanolamine are added. The completed prepolymer was dissolved with 390 g of acetone at 50° C. and then a solution of 4.9 g of isophoronediamine in 8.7 g of acetone and, after 5 minutes, 0.1 g of ethylenediamine in 0.6 g of water was metered in. Subsequent stirring time was 10 minutes. Thereafter 35.3 g of 1-normal hydrochloric acid were added and after a further 5 minutes, over the course of 10 minutes, dispersion was carried out by addition of 880 g of water. The solvent was then removed by vacuum distillation to give a storage-stable dispersion having a solids content of 30%, a particle size of 149 nm and a viscosity of <50 mPas. A maximum of 27.1% of PB 3.5 could be dissolved in the dispersion.

Example 5

Preparation of Aqueous Polyurethane Dispersion PUD5

70.0 g of PolyTHF 1000, 326.7 g of PolyTHF 2000, 22.9 g of neopentyl glycol, and 42.7 g of Polyether LB 25 were heated to 70° C. Then, at 70° C. over the course of 5 minutes, a mixture of 53.8 g of hexamethylene diisocyanate and 71.1 g of isophorone diisocyanate were added and the mixture was stirred until the NCO value was below the theoretical value. Thereafter, at 70° C., 9.2 g of N-methyldiethanolamine were added. The completed prepolymer was dissolved with 600 g of acetone at 50° C., and then a solution of 13.7 g of isophoronediamine in 24.3 g of acetone was metered in. The subsequent stirring time was 10 minutes. Thereafter 73.2 g of 1-normal hydrochloric acid were added and after a further 5 minutes, over the course of 10 minutes, dispersion was carried out by addition of 1350 g of water. This was followed by the removal of the solvent by vacuum distillation to give a storage-stable dispersion having a solids content of 30%, a particle size of 301 nm, and a viscosity of <50 mPas.

The examples which follow demonstrate the preparation of silane-terminated prepolymers.

Example 6

Preparing Silane-Terminated Prepolymer STP1

A mixture of 1000 g HDI and 1 g of benzoyl chloride was admixed dropwise at 80° C. over the course of 3 hours with 1000 g of a polyalkylene oxide having a molar mass of 4680 g/mol, prepared starting from glycerol, with an ethylene oxide weight fraction of 71% and a propylene oxide weight fraction of 26%, dried beforehand under a pressure of 0.1 mbar and at 100° C. for 6 hours, this dropwise addition being followed by stirring for 12 hours. The excess HDI was removed by thin-film distillation at 130° C. and 0.1 mbar. This gave a prepolymer having an NCO content of 2.42% and a viscosity of 3500 mPas.

200 g of the resulting prepolymer were subsequently admixed at 30-40° C. over the course of 10 minutes with 31.7 g of Geniosil XL 926. After a further 60 minutes of stirring at 30° C., complete conversion of the NCO prepolymer to the STP was detectable by IR spectroscopy. This gave a viscous, colorless liquid.

Example 7

Preparing Silane-Terminated Prepolymer STP2

390 g of Desmodur N 3300 were admixed dropwise at 80° C. with 1125 g of a polyalkylene oxide having a molar mass of 2250 g/mol, prepared starting from butyl diglycol and with an ethylene oxide weight fraction of 79% and a propylene oxide weight fraction of 14%, dried beforehand at 100° C. for 2 hours under a pressure of 0.1 mbar, and the dropwise addition was followed by stirring at 80° C. until the NCO content of 3.67% was reached.

5.0 g of the resulting prepolymer were subsequently admixed at room temperature over the course of 10 minutes with 1.2 g of Geniosil XL 926. After a further 30 minutes of stirring, complete conversion of the NCO prepolymer to the STP was detectable by IR spectroscopy. This gave a viscous, colorless liquid.

Example 8

Preparing Silane-Terminated Prepolymer STP3

490 g of Desmodur XP 2599 were admixed dropwise at 80° C. with 394 g of a polyalkylene oxide having a molar mass of 2250 g/mol, prepared starting from butyl diglycol and with an ethylene oxide weight fraction of 79% and a propylene oxide weight fraction of 14%, dried beforehand at 100° C. for 2 hours under a pressure of 0.1 mbar, and the dropwise addition was followed by stirring at 80° C. until the NCO content of 2.22% was reached.

A solution of 51.8 g of the resulting prepolymer in 70 g of dry diethyl ether was subsequently admixed at room temperature over the course of 10 minutes with 7.5 g of Geniosil XL 926. After a further 30 minutes of stirring, complete conversion of the NCO prepolymer to the STP was detectable by IR spectroscopy. This gave a viscous, colorless liquid.

Example 9

Preparing Silane-Terminated Prepolymer STP4

A solution of 50 g of Desmodur XP 2617 in 55 g of dry acetone was admixed at 30° C. over the course of 30 minutes with 42 g of Geniosil XL 926. After a further 30 minutes of stirring at 40° C., complete conversion of the NCO prepolymer to the STP was detected by IR spectroscopy. This gave a viscous, colorless liquid.

Example 10

Preparing Silane-Terminated Prepolymer STP5

A mixture of 800 g of a polyalkylene oxide having a molar mass of 2000 g/mol, prepared starting from 1,2-propylene glycol, and with an ethylene oxide weight fraction of 47% and a propylene oxide weight fraction of 49%, dried beforehand under a pressure of 0.1 mbar at 80° C. for 1 hour, and 2.8 g of benzoyl chloride was admixed dropwise at 80° C. over the course of 45 minutes with 1000 g of HDI, followed by stirring for 2 hours. The excess HDI was removed by thin-film distillation at 130° C. and 0.4 mbar. This gave a prepolymer having an NCO content of 3.43% and a viscosity of 1250 mPas.

498 g of the resulting prepolymer were subsequently admixed at 30-40° C. over the course of 15 minutes with 104.5 g of Geniosil XL 926. After a further 60 minutes of stirring at 30° C., complete conversion of the NCO prepolymer to the STP was detectable by IR spectroscopy. The resulting STP had a higher viscosity compared to the NCO prepolymer used.

Example 11

Preparing Silane-Terminated Prepolymer STP6

A mixture of 1032 g of a polyalkylene oxide having a molar mass of 4000 g/mol, prepared starting from 1,2-propylene glycol, and with an ethylene oxide weight fraction of 13% and a propylene oxide weight fraction of 86%, dried beforehand under a pressure of 0.1 mbar at 80° C. for 1 hour, and 1.8 g of benzoyl chloride was admixed dropwise at 80° C. over the course of 30 minutes with 650 g of HDI, followed by stirring for 4 hours. The excess HDI was removed by thin-film distillation at 130° C. and 0.03 mbar. This gave a prepolymer having an NCO content of 1.82% and a viscosity of 2100 mPas.

207.5 g of the resulting prepolymer were subsequently admixed at 30-40° C. over the course of 15 minutes with 24.8 g of Geniosil XL 926. After a further 30 minutes of stirring at 30° C., complete conversion of the NCO prepolymer to the STP was detectable by IR spectroscopy. The resulting STP had a higher viscosity compared to the NCO prepolymer used.

Example 12

Preparing Silane-Terminated Prepolymer STP7

A mixture of 398 g of a polyalkylene oxide having a molar mass of 4800 g/mol, prepared starting from glycerol, and with an ethylene oxide weight fraction of 13% and a propylene oxide weight fraction of 85%, dried beforehand under a pressure of 0.1 mbar at 80° C. for 1 hour, and 0.7 g of benzoyl chloride was admixed dropwise at 80° C. over the course of 30 minutes with 315 g of HDI, followed by stirring for 2 hours. The excess HDI was removed by thin-film distillation at 140° C. and 0.07 mbar. This gave a prepolymer having an NCO content of 2.10%.

200 g of the resulting prepolymer were subsequently admixed at 30-40° C. over the course of 10 minutes with 27.6 g of Geniosil XL 926. After a further 60 minutes of stirring at 30° C., complete conversion of the NCO prepolymer to the STP was detectable by IR spectroscopy. This gave a viscous, colorless liquid.

Example 13

Preparing Silane-Terminated Prepolymer STP8

A mixture of 201 g of a polyalkylene oxide having a molar mass of 1000 g/mol, prepared starting from 1,2-propylene glycol, and with a propylene oxide weight fraction of 92%, dried beforehand under a pressure of 0.1 mbar at 80° C. for 1 hour, and 0.8 g of benzoyl chloride was admixed dropwise at 80° C. over the course of 30 minutes with 588 g of HDI, followed by stirring for 2 hours. The excess HDI was removed by thin-film distillation at 140° C. and 0.05 mbar. This gave a prepolymer having an NCO content of 6.09%.

200 g of the resulting prepolymer were subsequently admixed at 30-40° C. over the course of 10 minutes with 80 g of Geniosil XL 926. After a further 60 minutes of stirring at 30° C., complete conversion of the NCO prepolymer to the STP was detectable by IR spectroscopy. This gave a viscous, colorless liquid.

Example 14

Preparing Silane-Terminated Prepolymer STP9

A mixture of 189 g of a polyesterpolyol based on diethylene glycol and adipic acid having a molar mass of 1000 g/mol, dried beforehand under a pressure of 5 mbar at 80° C. for 30 minutes, and 0.9 g of benzoyl chloride was admixed dropwise at 70-80° C. over the course of 40 minutes with 477 g of HDI, followed by stirring for 2 hours. The excess HDI was removed by thin-film distillation at 140° C. and 0.05 mbar. This gave a prepolymer having an NCO content of 5.81% and a viscosity of 6100 mPas.

160 g of the resulting prepolymer were subsequently admixed at 30-40° C. over the course of 15 minutes with 61 g of Geniosil XL 926. After a further 30 minutes of stirring at 30° C., complete conversion of the NCO prepolymer to the STP was detectable by IR spectroscopy. This gave a viscous, colorless liquid.

Example 15

Preparing Silane-Terminated Prepolymer STP10

A mixture of 423 g of a polyalkylene oxide having a molar mass of 3825 g/mol, prepared starting from trimethylolpropane, and with an ethylene oxide weight fraction of 13% and a propylene oxide weight fraction of 83%, dried beforehand under a pressure of 0.1 mbar at 80° C. for 1 hour, and 0.8 g of benzoyl chloride was admixed dropwise at 80° C. over the course of 30 minutes with 420 g of HDI, followed by stirring for 2 hours. The excess HDI was removed by thin-film distillation at 130° C. and 0.03 mbar. This gave a prepolymer having an NCO content of 2.84%.

200 g of the resulting prepolymer were subsequently admixed at 30-40° C. over the course of 10 minutes with 37 g of Geniosil XL 926. After a further 60 minutes of stirring at 30° C., complete conversion of the NCO prepolymer to the STP was detectable by IR spectroscopy. This gave a viscous, colorless liquid.

Example 16

Preparing Silane-Terminated Prepolymer STP11

A mixture of 270 g of the NCO prepolymer prepared according to Example 10 and 1349 g of the NCO prepolymer prepared according to Example 11 was admixed dropwise at 30-40° C. over the course of 30 minutes with 217 g of Geniosil XL 926, and the product was stirred at 30° C. for a further 30 minutes. Complete conversion of the NCO prepolymer to the STP was detected by IR spectroscopy. The product was a viscous, colorless liquid.

In the subsequent experiments, the results of the curing tests on the foams are depicted.

Example 17

Curing of STP and PUD as a Foam 38.6 g of DME and 4.3 g of P/B 3.5 were dissolved in 100 g of prepolymer STP1.
1.2 g of P/B 3.5 were dissolved in 40 g of PUD5.
The two components were each individually introduced into one chamber, respectively, of a 2K spraying apparatus operated by compressed air. Synchronous delivery of both components in the volume ratio 2.5 (STP):1 (PUD) took place via a static mixer in which commixing took place. With foaming and complete curing within about 60 seconds, a colorless, elastic, fine-cell foam was obtained.

Example 18

Curing of STP and PUD as a Foam 26.6 g of n-butane were dissolved in 100 g of prepolymer STP11. 1.2 g of P/B 3.5 were dissolved in 40 g of PUD5.
The two components were each individually introduced into one chamber, respectively, of a 2K spraying apparatus operated by compressed air. Synchronous delivery of both components in the volume ratio 2.5 (STP):1 (PUD) took place via a static mixer in which commixing took place. With foaming and complete curing within about 10 seconds, a colorless, elastic, fine-cell foam was obtained.

Example 19

Curing of STP and PUD as a Foam 44.9 g of DME were dissolved in 100 g of prepolymer STP9. 1.2 g of P/B 3.5 were dissolved in 40 g of PUD5.
The two components were each individually introduced into one chamber, respectively, of a 2K spraying apparatus operated by compressed air. Synchronous delivery of both components in the volume ratio 2.5 (STP):1 (PUD) took place via a static mixer in which commixing took place. With foaming and complete curing within about 30 seconds, a colorless, elastic foam was obtained.

Example 20

Curing of STP and PUD as a Foam 40.8 g of P/B 3.5 were dissolved in 100 g of prepolymer STP11. 40 g of PUD5 were used without gassing.
The two components were each individually introduced into one chamber, respectively, of a 2K spraying apparatus operated by compressed air. Synchronous delivery of both components in the volume ratio 2.5 (STP):1 (PUD) took place via a static mixer in which commixing took place. With foaming and complete curing within about 5 seconds, a colorless, elastic, fine-cell foam was obtained.

Example 21

Curing of STP and PUD as a Foam 31.6 g of DME were dissolved in 100 g of prepolymer STP5. 3.1 g of P/B 3.5 were dissolved in 40 g of PUD 1, which had been adjusted beforehand using citric acid to a pH of 5.5.
The two components were each individually introduced into one chamber, respectively, of a 2K spraying apparatus operated by compressed air. Synchronous delivery of both components in the volume ratio 2.5 (STP):1 (PUD) took place via a static mixer in which commixing took place. With foaming and complete curing within about 60 seconds, an elastic compact foam with a filmed surface was obtained.

These examples demonstrate that starting from a variety of original substances, i.e. polyurethane dispersions and silane prepolymers, it is possible to produce a multiplicity of different foams. And yet the compositions can be used not only for producing foams, but also, as shown by the following examples, as a starting basis for the production of casting compositions.

Example 22

Curing of STP and PUD as Casting Composition 100 g of prepolymer STP11 and 33 g of PUD1 were rapidly stirred with one another and applied to release paper in a layer thickness of approximately 6 mm. The material, which has a high viscosity after just 10 seconds, was cured fully within 30 seconds. This gave a compact cast material having an elongation at break of 35%.

Comparative Example According to EP 1 829 908, Example 1

The aim with this comparative experiment is to compare the inventive function of the polyurethane dispersion with the 2K systems known from the prior art—in the present case, with Example 1 of EP 1 829 908. No P/B 3.5 propellant gas could be dissolved in component 2 (8 parts water, 13 parts citric acid) in this case. On account of this fact, this composition cannot be satisfactorily delivered from the 2K spraying apparatus, since it was not possible to set exactly the mixing proportions between the prepolymer component and the aqueous component, and since it was not possible to achieve sufficient foaming of the mixture, either.

The invention claimed is:

1. An isocyanate-free multicomponent system comprising at least two separate components, the first component comprising at least one alkoxysilane-terminated prepolymer and the second component comprising an aqueous component, with the aqueous component comprising a polyurethane dispersion comprising 5 to 65 wt % of polyurethane based on the total weight of the polyurethane dispersion, wherein the alkoxysilane-terminated prepolymer comprises an alkoxysilane-terminated polyurethane prepolymer and an isocyanate-terminated prepolymer, wherein the alkoxysilane-terminated polyurethane prepolymer is prepared from an [(cyclohexylamino)methyl]triethoxysilane and an isocyanate-terminated prepolymer, and wherein the isocyanate-terminated prepolymer is prepared from a polyol and an aliphatic polyisocyanate, wherein the first and the second component of the multicomponent system are present in a volume ratio of 2:1 to 3:1 to one another.

2. The multicomponent system as claimed in claim 1, wherein the alkoxysilane-terminated polyurethane prepolymer comprises a polyesterpolyol and/or polyetherpolyol, the fraction of ethylene oxide units in the polyetherpolyol being not more than 50 wt %.

3. The multicomponent system as claimed in claim 1, wherein the weight average of the alkoxysilane-terminated prepolymer is 500 to 20 000 g/mol.

4. The multicomponent system as claimed in claim 1, wherein the polyurethane dispersion comprises 20 to 60 wt % of polyurethane.

5. The multicomponent system as claimed in claim 1, wherein the weight-average of the polyurethane in the polyurethane dispersion is 10 000 to 1 000 000 g/mol.

6. The multicomponent system as claimed in claim 1, wherein the polyurethane dispersion has a pH of between 5.0 and 9.0 at 20° C.

7. The multicomponent system as claimed in claim 1, wherein the first and/or the second component comprises an active medical ingredient selected from the group consisting of substances that release nitrogen monoxide under in vivo conditions, vitamins, provitamins, carotenoids, analgesics, antiseptics, hemostyptics, antihistamines, antimicrobial metals or salts thereof, plant-based wound healing promoter substances, plant extracts, enzymes, growth factors, enzyme inhibitors, and combinations thereof.

8. The multicomponent system as claimed in claim 1, wherein the first and the second component of the multicomponent system are present in a volume ratio of about 2.5:1 to one another.

9. The multicomponent system as claimed in claim 1, wherein the first and/or the second component comprises in each case a propellant gas.

* * * * *